(12) United States Patent
Vijay et al.

(10) Patent No.: US 11,751,863 B2
(45) Date of Patent: *Sep. 12, 2023

(54) MULTI-SUTURE KNOTLESS ANCHOR FOR ATTACHING TISSUE TO BONE AND RELATED METHOD

(71) Applicant: ArthroCare Corporation, Austin, TX (US)

(72) Inventors: Francis Vijay, Irvine, CA (US); George W. White, Corona, CA (US)

(73) Assignee: ArthroCare Corporation, Austin, TX (US)

( * ) Notice: Subject to any disclaimer, the term of this patent is extended or adjusted under 35 U.S.C. 154(b) by 496 days.

This patent is subject to a terminal disclaimer.

(21) Appl. No.: 16/675,697

(22) Filed: Nov. 6, 2019

(65) Prior Publication Data

US 2020/0085423 A1 Mar. 19, 2020

Related U.S. Application Data

(60) Continuation of application No. 15/587,714, filed on May 5, 2017, now Pat. No. 10,492,775, which is a division of application No. 13/441,055, filed on Apr. 6, 2012, now Pat. No. 9,855,028.

(51) Int. Cl.
*A61B 17/04* (2006.01)

(52) U.S. Cl.
CPC .. *A61B 17/0401* (2013.01); *A61B 2017/0403* (2013.01); *A61B 2017/045* (2013.01); *A61B 2017/0409* (2013.01); *A61B 2017/0414* (2013.01); *A61B 2017/0424* (2013.01); *A61B 2017/0427* (2013.01); *A61B 2017/0438* (2013.01); *A61B 2017/0446* (2013.01)

(58) Field of Classification Search
CPC ........ A61B 17/0401; A61B 2017/0403; A61B 2017/0409; A61B 2017/0414; A61B 2017/0424; A61B 2017/0427; A61B 2017/0438; A61B 2017/0446; A61B 2017/045

See application file for complete search history.

(56) References Cited

U.S. PATENT DOCUMENTS

| | | | | |
|---|---|---|---|---|
| 5,649,963 A | * | 7/1997 | McDevitt | F16B 13/0866 606/313 |
| 2003/0109900 A1 | * | 6/2003 | Martinek | A61F 2/0811 606/219 |
| 2006/0030884 A1 | * | 2/2006 | Yeung | A61B 17/0467 606/232 |
| 2008/0051836 A1 | * | 2/2008 | Foerster | A61B 17/0401 606/232 |

(Continued)

*Primary Examiner* — Richard G Louis
(74) *Attorney, Agent, or Firm* — Norman F. Hainer, Jr.; Kate Ryland Tetzlaff

(57) ABSTRACT

A multi-suture knotless anchor and related method for securing soft tissue, such as tendons, to bone are described. The suture anchor includes a body, a sleeve, and an outer deformable bone locking structure. The bone locking structure has a first low profile configuration for insertion into the bone, and a second larger profile configuration for engaging the bone when actuated. The bone anchor and methods permit a suture attachment that lies beneath the cortical bone surface and does not require tying of knots in the suture.

20 Claims, 11 Drawing Sheets

(56) References Cited

U.S. PATENT DOCUMENTS

| | | | |
|---|---|---|---|
| 2009/0248068 A1* | 10/2009 | Lombardo | A61F 2/0811 606/232 |
| 2010/0082045 A1* | 4/2010 | Petersen | A61B 17/0401 606/232 |
| 2010/0198258 A1* | 8/2010 | Heaven | A61B 17/0401 606/232 |
| 2011/0004242 A1* | 1/2011 | Stchur | A61B 17/0401 606/232 |

* cited by examiner

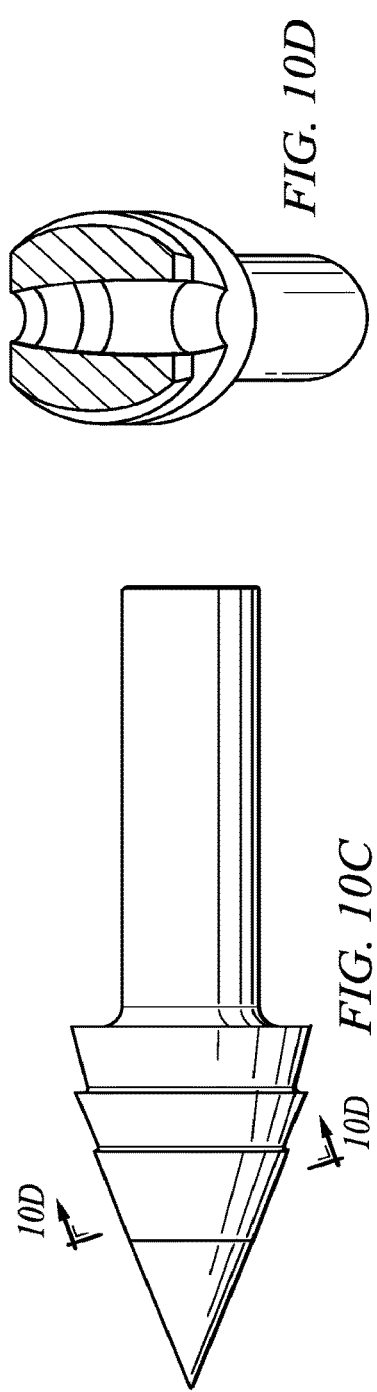
FIG. 10C
FIG. 10D
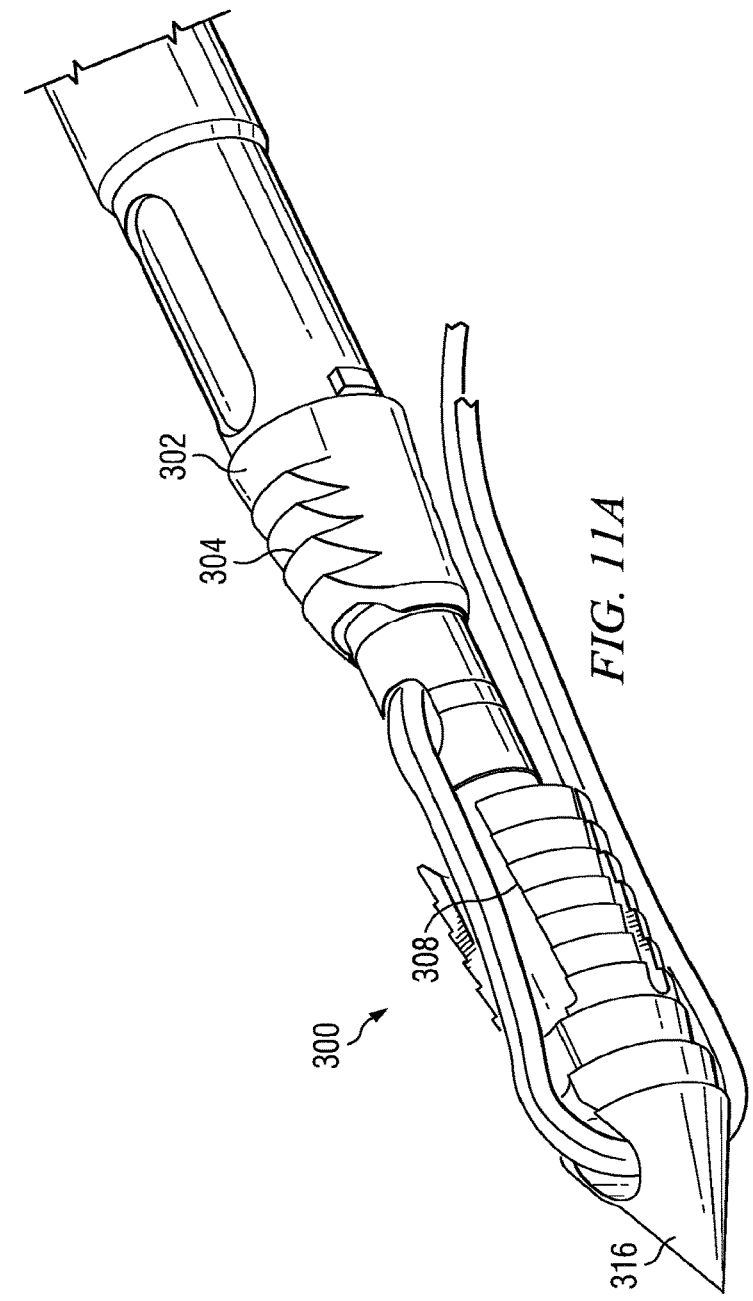
FIG. 11A

MULTI-SUTURE KNOTLESS ANCHOR FOR ATTACHING TISSUE TO BONE AND RELATED METHOD

CROSS-REFERENCE TO RELATED APPLICATIONS

This application is a continuation of U.S. patent application Ser. No. 15/587,714 filed May 5, 2017, which is a divisional of U.S. patent application Ser. No. 13/441,055 filed Apr. 6, 2012, the entirety of which is incorporated herein by reference in its entirety.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching soft tissue in a minimally invasive procedure.

Less invasive arthroscopic techniques are continuing to be developed in an effort to address the shortcomings of open surgical repair. Working through small trocar portals allow surgeons to cause less trauma than an open procedure. However, less invasive techniques present unique challenges as the surgeon has less space to manipulate tools and implants.

Unfortunately, the skill level required to facilitate entirely arthroscopic repair tissue is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of certain procedures the knot bundle left in the tissue can be felt by the patient postoperatively when the patient exercises the joint. Often the knots tied arthroscopically are difficult to achieve, impossible to adjust, and are located in less than optimal areas of the shoulder. Suture tension is also impossible to measure and adjust once the knot has been fixed.

Another significant difficulty with current arthroscopic repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, and somewhat vascular interior of the bone). The cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90 degrees so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 issued to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 issued to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 issued to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrote the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be compromised.

A disclosure that incorporates bone attachment and eliminates knot tying is set forth in U.S. Pat. No. 5,702,397 issued to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

PCT Publication WO 01/10312 by McDevitt et al. also describes a self-locking suture anchor for attaching soft tissue to bone. In this device a tissue anchor holds a filament within the anchor so that an applied force greater than a threshold force causes the filament to move longitudinally, while an applied force that is less than the threshold force does not move the filament.

U.S. Patent Publication No. 2008/0051836 by Foerster et al. describes knotless bone anchor body having an outer rigid anchoring structure and an interior lumen. The lumen is sized to receive a locking plug and to compress and lock a suture situated therein.

A number of the suture anchors described above have static or fixed barbed anchor designs. Namely, the outer diameter of the anchoring structure is fixed (or constant) irrespective of the bone quality. This is a disadvantage when the bone is relatively soft. The anchor may have a tendency to pull out.

Despite the above, a new approach is desired for repairing or fixing soft tissues to bone. In particular a new approach is desired that embeds a suture anchor below the cortical bone surface, utilizes multiple sutures, and is knotless.

SUMMARY OF THE INVENTION

A suture anchor for securing a soft tissue to a bone with at least one suture comprises a first undeployed configuration in which tissue may be drawn towards the suture anchor by applying tension to a free limb of the suture, and a second deployed configuration in which the suture anchor is fixed in the bone and the suture is locked in the suture anchor thereby securing the tissue to the bone. The suture anchor includes: an anchor body having a proximal section, an elongate intermediate section, and a distal section; a bone locking member at least partially disposed about the elongate intermediate section and forming a cavity between an inner surface of the bone locking member and an outer surface of the elongate intermediate section. The suture anchor also includes a sleeve member which moveably cooperates with the anchor body and the bone locking member to slide into the cavity along the elongate intermediate section thereby expanding the bone locking member and compressing the at least one suture between the outer surface of the elongate intermediate section and an inner surface of the sleeve member. The shape of the cavity may vary. In one embodiment the cavity has an annular shape.

In another embodiment, the bone locking member comprises a plurality of deflecting sections which deflect outwardly from the anchor body when the sleeve member is urged into the cavity. The plurality of deflecting sections may comprise wings. In one embodiment, the plurality of wings comprise at least three discrete wings.

In another embodiment, the suture anchor comprises a bone piercing tip. The bone piercing tip may taper from a proximal base to a distal end. The base may have an outer diameter of at least 4 mm.

In another embodiment the suture anchor body comprises a suture guide which guides the suture from one side of the anchor body to the other side of the anchor body. The suture guide may be an aperture extending through the distal section of the anchor body.

In another embodiment, the suture anchor comprises ridges which engage the bone to hold the anchor in the bone. The ridges may be situated on the bone locking member and/or the sleeve. Additionally, the distal section of the anchor body may comprise ridges.

The suture anchor may be formed of various materials. In one embodiment, the suture anchor is formed of a biocompatible polymer.

In another embodiment a knotless suture anchoring system for anchoring a length of suture with respect to a bone comprises: an anchor insertion instrument comprising a handle, and an elongate rigid shaft extending distally from the handle; an anchor body detachably connected to the instrument elongate rigid shaft. The anchor body comprising a suture carrying portion allowing the suture to pass from a first side of the anchor body to an opposite side of the anchor body. The anchoring system further comprising a bone locking member disposed on the anchor body. In embodiments, the bone locking member comprises a bone anchoring structure extending from a base and radially spaced from the intermediate section of the anchor body such that a cavity is defined between an outer surface of the anchor body and the inner surface of the bone anchoring structure. The cavity is sufficient in size to allow the length of suture to be drawn through the cavity and to the suture carrying portion. The anchoring system also includes a sleeve member slidably disposed on the shaft distal end section of the instrument and proximal to the anchor body. The sleeve member has an outer diameter sufficient in size and shape to radially expand the anchoring structure when pushed along the shaft distal end section and into the cavity, and the sleeve member having an inner diameter sufficient in size and shape to compress a length of suture between the anchor body and an inner surface of the sleeve.

In another embodiment the system comprises a snare extending through at least a portion of the insertion instrument and the suture carrying portion of the anchor bone such that when a distal portion of the snare is affixed to the suture, withdrawal of the snare pulls the suture through the suture carrying portion of the anchor body and the distal portion of the insertion instrument.

In another embodiment, the distal end section of the anchor comprises a pointed tip.

In another embodiment, the system includes a section of tensile weakness or engineered notch along the instrument shaft permitting the shaft to be detached from the anchor body proximal end upon application of a predetermined tensile force on the shaft in the proximal direction.

In another embodiment a method for knotless securing of soft tissue to bone comprises stitching tissue with at least one suture; loading an anchor assembly with the at least one suture, the anchor assembly being detachably connected to the end of an insertion instrument; manipulating the anchor assembly into the bone; tensioning a free end of the suture to approximate the tissue to the anchor assembly; moving a sleeve member into the anchor assembly to deploy a bone locking structure of the anchor assembly and to compress the suture; and retracting the insertion instrument leaving the anchor assembly embedded in the bone, and the tissue secured to the bone.

In another embodiment loading the anchor assembly with the at least one suture comprises loading the anchor assembly with a plurality of sutures.

In another embodiment loading the anchor assembly is performed by snaring the sutures. Snaring may be performed by inserting the lengths of the sutures in a wire loop of a snare device detachably affixed to the distal section of the shaft, and pulling on a snare grip to draw the sutures through the anchor assembly and the instrument.

In another embodiment manipulating the anchor and suture into a bone comprises hammering the proximal end of the insertion instrument. Also, in embodiments, the tensioning is performed prior to the manipulating step. The tensioning may be performed semi-automatically In another embodiment the tissue is a rotator cuff tendon and the bone is the humeral head.

In another embodiment the moving step includes compressing a first section of suture between the anchor body and the sleeve member and a second section of the suture between a bone surface and an exterior of the bone locking structure. The moving step may include pushing the sleeve into the cavity until a stop on the anchor body prevents further movement.

In another embodiment, the method comprises toggling the anchor assembly to a tilt angle. The toggling may be performed by applying tension on the tissue side of the suture.

The invention, together with additional features and advantages thereof, may best be understood by reference to the following description taken in conjunction with the accompanying illustrative drawings.

BRIEF DESCRIPTION OF THE DRAWINGS

FIGS. 10A-10D are various views of another plug component of a suture anchor assembly;

FIGS. 11A-11C are perspective views of another suture anchor transitioning from a first undeployed configuration, to an intermediate configuration, and to a deployed or locked configuration respectively;

DETAILED DESCRIPTION

Figure 1A:
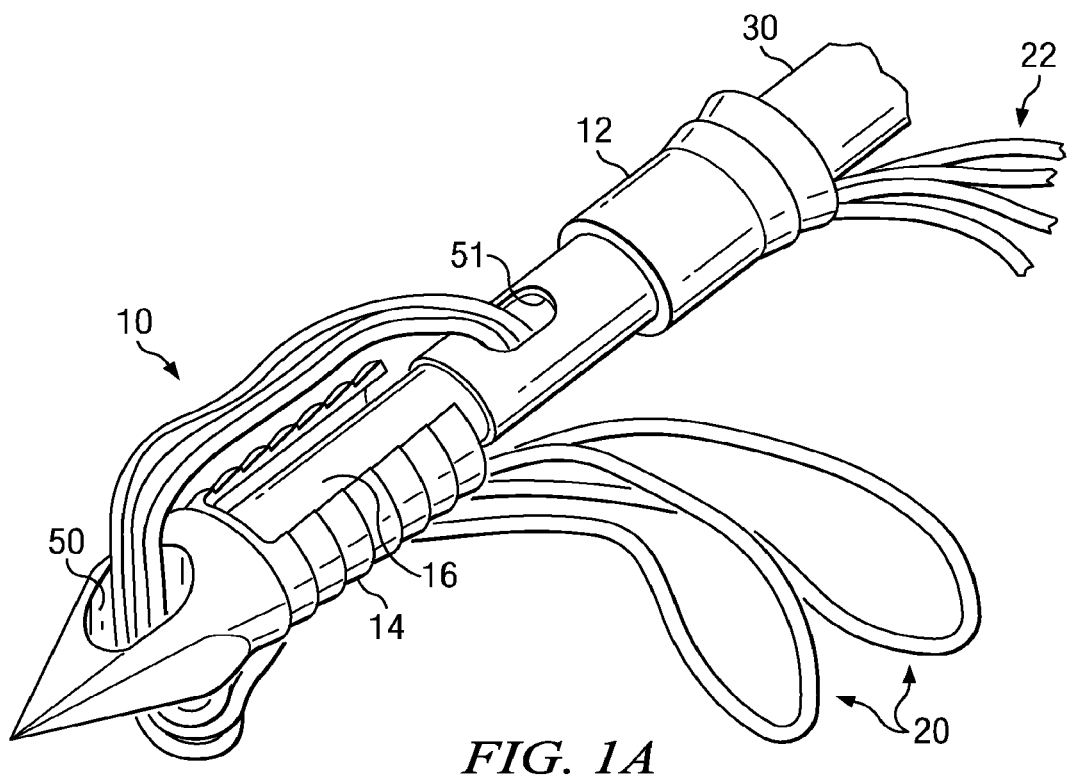
FIG. 1A is a perspective view of a suture anchor in an undeployed configuration.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

The present invention provides improved methods and devices for knotless suturing of tissue. Although the variation discussed herein discusses use of a suture, the term "suture" may include any piece of material that is used to close a wound or connect tissue (e.g., catgut, thread, wire, etc.) so long as the material can be used with the other portions of the anchor as described herein. Accordingly, sutures as described herein may include polymeric, metallic, or other types of sutures.

For illustrative purposes, the examples discussed herein show the use of the anchoring system to suture soft tissue to a bone structure, namely, the humeral head. The present invention is particularly well-suited for repairing rotator cuff injuries by re-attaching the rotator cuff tendon to the outside of the humeral head. Embodiments of the present invention permit minimally invasive surgeries on such injuries and greatly facilitate rapid and secure fixation of the rotator cuff tendon to the humeral head. However, it should be understood that the same principles described herein apply to the repair of other injuries in which soft tissue is to be re-attached to a bone structure or other tissue region. For example, in embodiments, the soft labrum may be attached to the glenoid. In other embodiments, other soft or connective tissues are attached to bone bodies or other tissues as the case may be.

Anchor Structure Overview

Figure 1B:
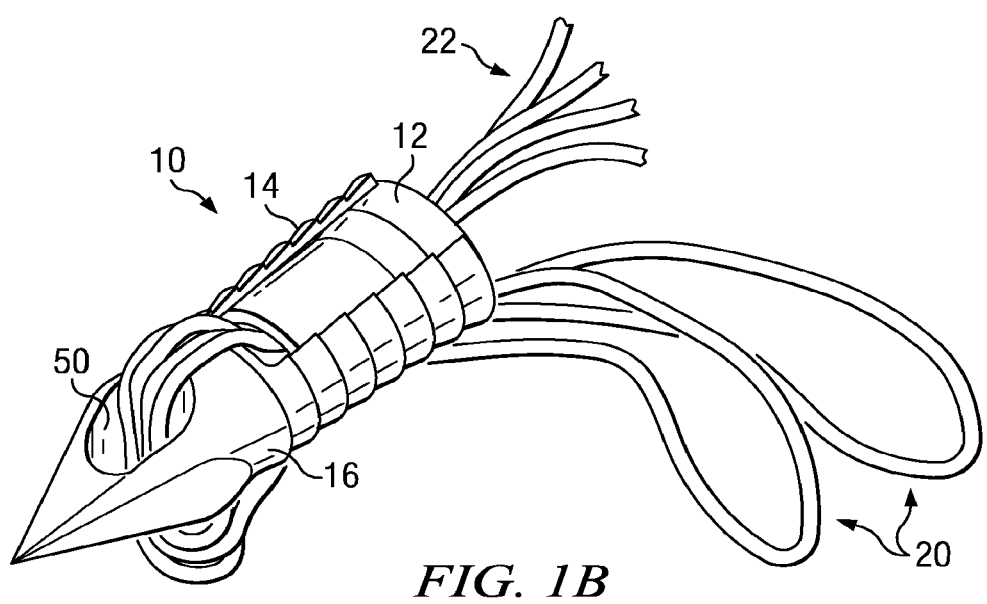
FIG. 1B is a perspective view of the suture anchor shown in FIG. 1A in a deployed configuration.
Figure 2A:
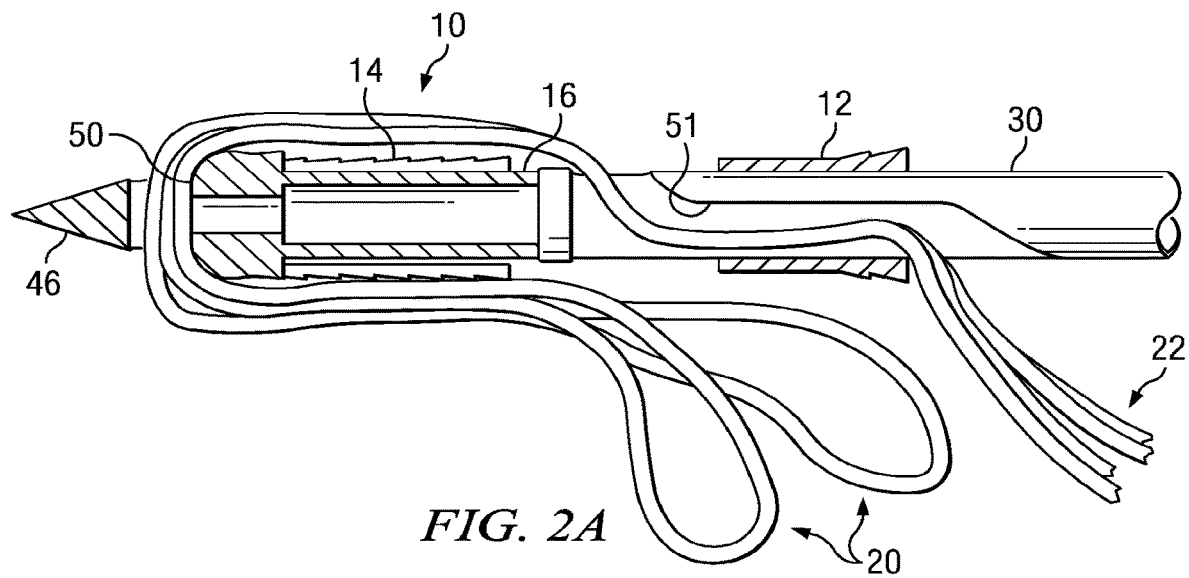
FIGS. 2A and 2B are sectional views of the suture anchor and insertion instrument shown in FIGS. 1A and 1B respectively.
Figure 2B:
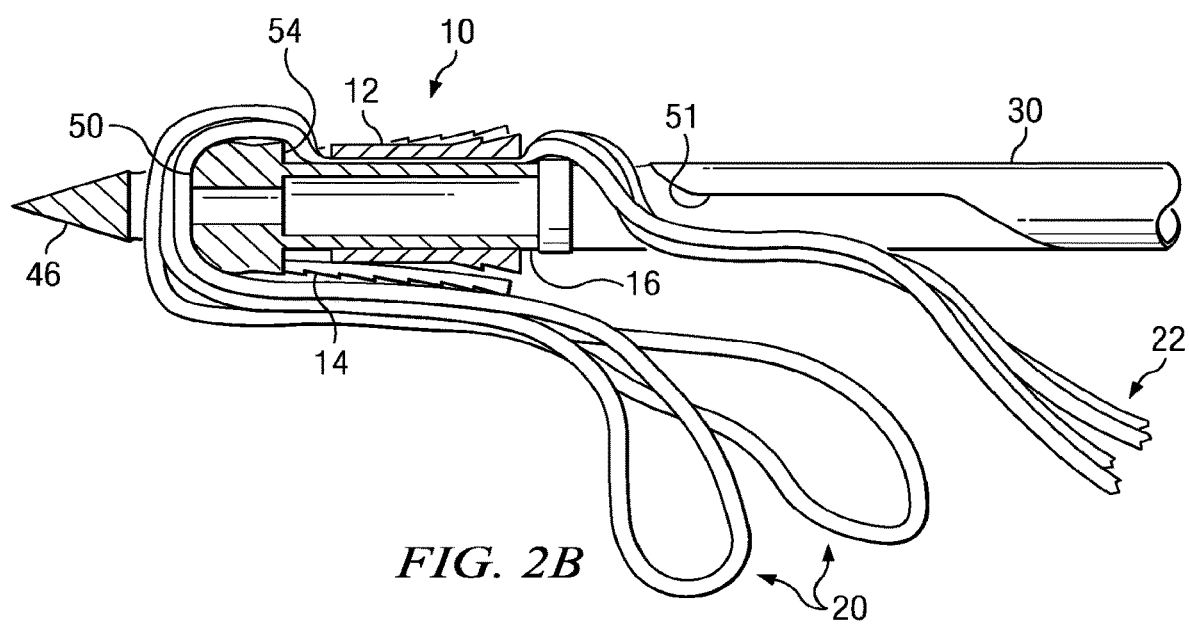

FIGS. 1A and 1B show an anchor assembly 10 for securing soft tissue to a bone with one or more sutures in an undeployed and deployed configuration respectively. FIGS. 2A and 2B show cross sectional views of the anchor shown in FIGS. 1A and 1B respectively. The anchor assembly 10 is shown comprising a plurality of components (namely, sleeve 12, wings 14, and body 16). The anchor components movably cooperate together to provide two configurations including: (a) a first undeployed configuration in which the tissue may be drawn towards the anchor by applying tension to the free ends or limbs of the suture; and (b) a second deployed configuration in which the anchor is fixed in the bone, and the suture is locked in the anchor thereby securing the tissue to the bone.

FIGS. 1A and 2A show the anchor assembly 10 in an undeployed configuration. In particular, sleeve member 12 is shown positioned proximal to wings 14, and anchor body 16. Wings 14 are undeformed, substantially parallel to the body 16, and unexpanded. In this undeployed state, it can be seen that the sutures are free to slide and move through the anchor upon applying a tension to either the tissue side 20 or the free side 22 of the sutures. In particular, the suture free legs 22 may be pulled so as to pull soft tissue attached to the bound legs 20 closer to the suture anchor.

Suture guide 50 may have an eyelet, groove, or slit shape. Preferably guide has a smooth surface to allow for easy suture sliding during use. Additionally, inner body 16 may have an elongate nest or groove (not shown) to provide some limitation to any lateral motion of the suture (i.e. to keep the suture from slipping off the shaft). The suture itself may also comprise a low friction material such as polyester suture to create an overall low friction environment. Examples of sutures include without limitation low friction UHMWPE suture and polyester suture.

At least one suture which includes at least one bound leg 20 is shown threaded through the eyelet 50 and redirected proximally back through the lumen 51 of the instrument 30 to result in free legs 22. The bound side or leg 20 is considered bound because in practice, this leg or limb of the suture is "bound" to the soft or connective tissues to be attached to the target tissue such as bone by virtue of passing the sutures through the connective or soft tissues using conventional suturing techniques known in the art. The free side or leg 22 is considered "free" because the surgeon or practitioner, in practice, has control over this limb or leg of the suture with his or her hands or appropriate instrumentation.

FIGS. 1B and 2B show the anchor assembly 10 in a deployed configuration. In particular, the sleeve 12 has been urged distally (e.g., pushed) by an instrument driver surface (not shown) onto the anchor body 16. As the sleeve is urged distally onto the anchor body 16, the outer surface of the sleeve 12 displaces wings 14, and in particular, radially expands the wings to embed, affix, or lock the anchor assembly in a bone.

The sleeve 12 also serves to lock or retain the suture. As the sleeve 12 is urged distally onto the anchor body 16, the inner surface of the sleeve compresses the suture against the outer surface of anchor body (or plug portion) 16 of the anchor assembly.

The embodiment shown in FIG. 2B also includes a second locking surface 54 which is off-axis, namely, not parallel to the longitudinal axis of the suture anchor body 16. The combination of contact surfaces to compress the suture aid to lock the suture and prevent slip. The combination of contact surfaces at angles to one another creates a tortuous path, increasing frictional forces on the suture when the anchor assembly is in the deployed configuration.

Additionally, in embodiments, the anchor assembly does not compress or deform the anchor body 16, nor the sleeve 12, and a gap (G) is present between the outer diameter of the anchor body 16 and the inner diameter of the sleeve 12. This gap allows for multiple sutures to be snared or threaded through the anchor assembly and attached to tissue. This gap ensures each of the suture lock and the bone lock function independently and effectively regardless of the number of sutures. This is an advantage of the present invention.

Anchor Body

Figure 3A:
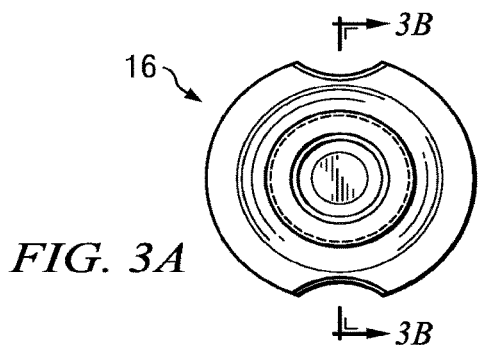
FIG. 3A is a proximal end view of a body component of a suture anchor.
Figure 3B:
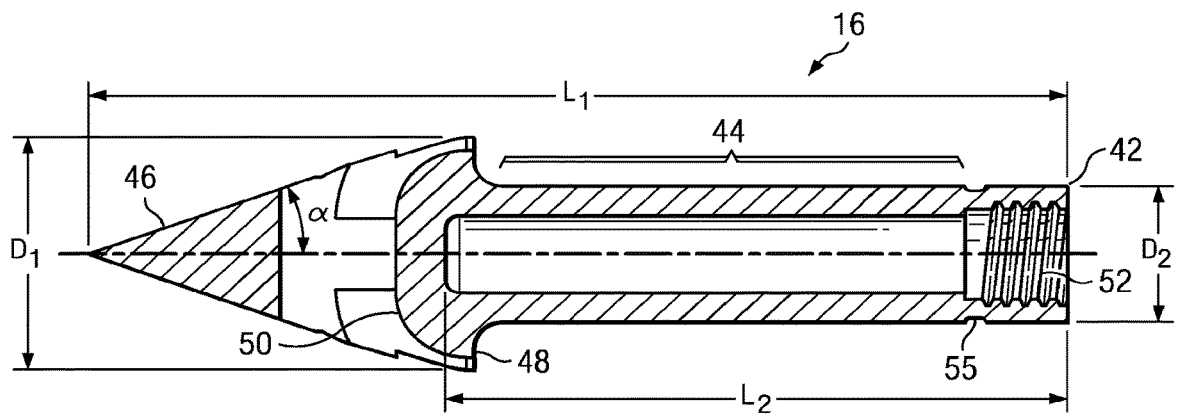
FIG. 3B is a sectional view of the body component taken along line 3B-3B of FIG. 3A.
Figure 4A:
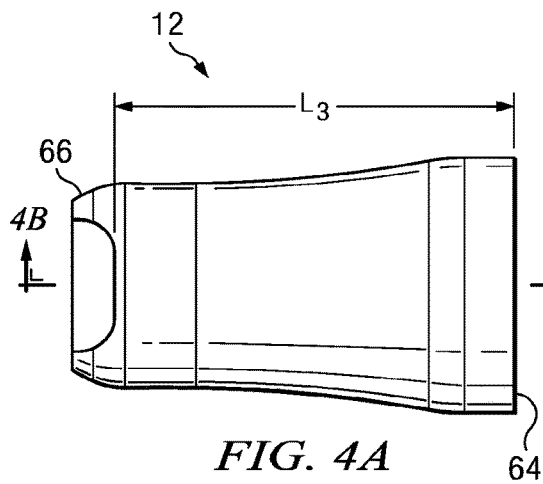
FIG. 4A is a side view of a sleeve component of a suture anchor.
Figure 4B:
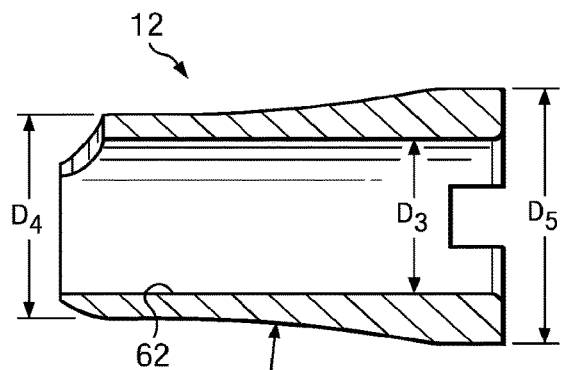
FIG. 4B is a sectional view of the sleeve component taken along line 4B-4B of FIG. 4A.
Figure 4C:
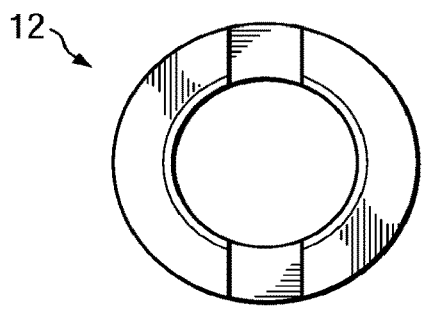
FIGS. 4C and 4D are proximal and distal end views respectively of the sleeve component shown in FIG. 4A.
Figure 4D:
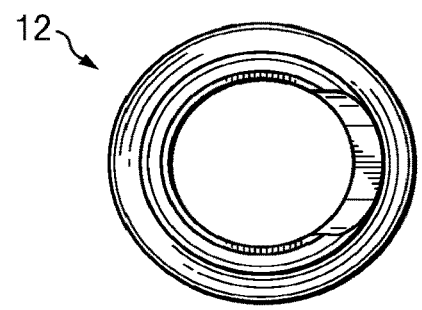
Figure 5A:
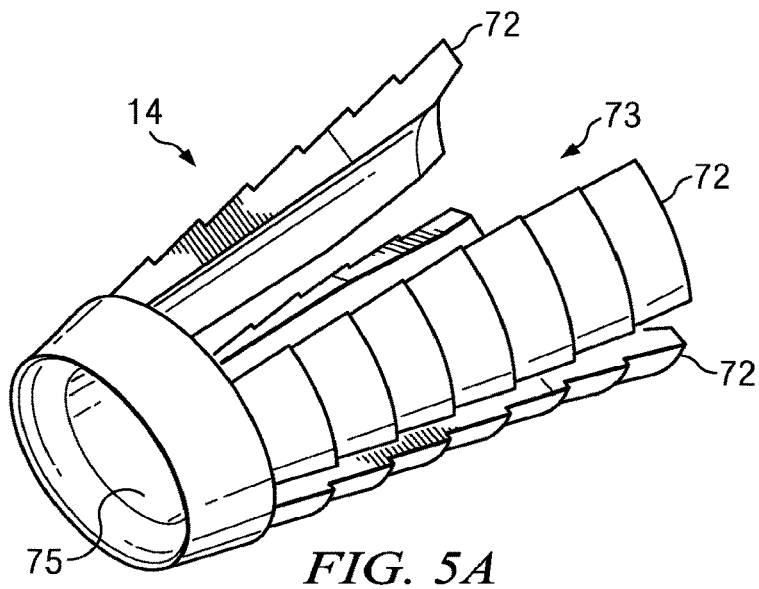
FIG. 5A is a perspective view of a bone locking component of a suture anchor.
Figure 5B:
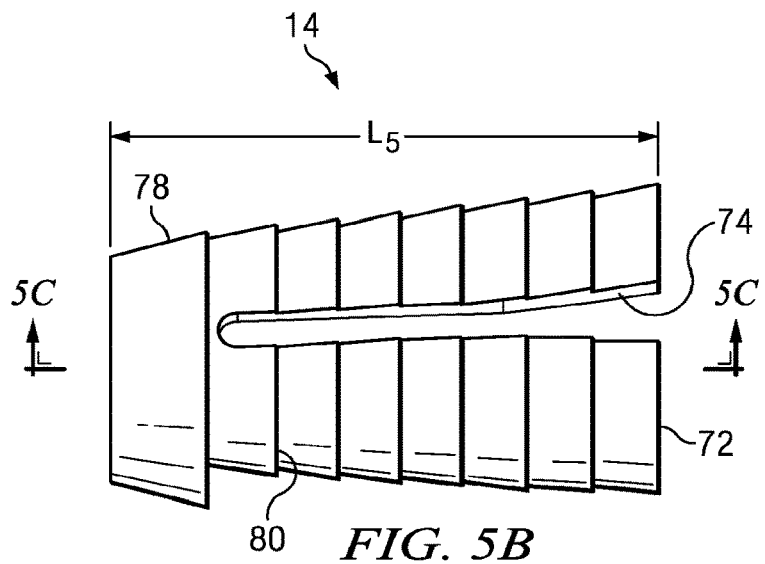
FIG. 5B is a side view of the bone locking component shown in FIG. 5A.
Figure 5C:
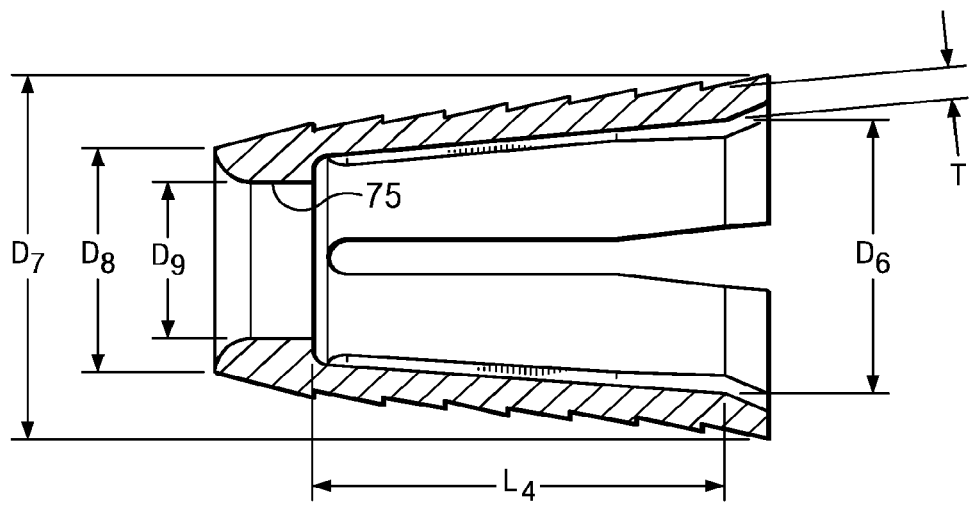
FIG. 5C is a sectional view of the bone locking component taken along line 5C-5C of FIG. 5B.
Figure 5D:
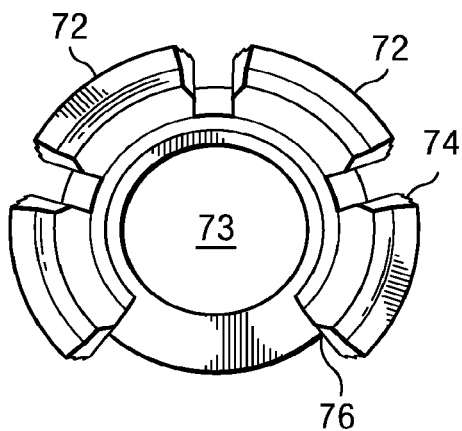
FIG. 5D is a proximal end view of the bone locking component of FIG. 5B.

FIGS. 3A and 3B show an anchor body or plug component 16 with the other components of the anchor assembly removed for clarity. The anchor body 16 is shown having a proximal section 42, an elongate intermediate section 44, and a tissue penetrating distal end section 46. An exemplary overall length (L1) of the plug component ranges from 0.55 to 0.75 inch and more preferably about 0.63 inch.

The distal end section 46 preferably is adapted to pierce bone. The piercing tip may facilitate the anchor to be pounded or driven into bone with a mallet or hammer-like instrument. The shape of the tip may vary widely. It may be solid, and comprise a sharp point. A dart shape is shown in FIG. 3B. The tip increases in diameter from the distal point at an angle ($\alpha$) from the centerline ranging from about 20 to 27 degrees and preferably about 23 degrees. The distal tip 46 increases in diameter from the distal to the proximal end until a maximum diameter is reached (D1) at the proximal end of the end section 46. Preferably, D1 ranges from 0.15 to 0.25 inch and more preferably from about 0.18 inch. However, the invention is intended only to be limited as recited in the appended claims.

The distal end section 46 also shows a suture holder or guide 50 which directs one or more sutures from one side of the suture anchor to the other side as shown, e.g., in FIGS. 1-2. The suture guide 50 may be in the form of an aperture or opening as shown. The aperture preferably has a diameter in the range of 0.060 to 0.080 inch. Additionally, the suture guide may comprise a groove or other shape which serves to guide the sutures into and out of the anchor assembly. The suture guide preferably is smooth so as to not damage the sutures nor provide friction when the suture is being loaded or the tissue approximated as will be discussed in more detail below.

The distal tip 46 may also comprise a coating or material to facilitate bone penetration. For example, the tip may be formed from a metal such as 316L stainless steel, or titanium, or a polymer such as PEEK. The anchor body including the tip may be formed of one material, or a combination of materials. In one embodiment, the anchor body is an injection molded biocompatible polymer such as PEEK. In another embodiment it is machined. Alternative embodiments may include a blunted tip for inserting into a prepared bone passage or a threaded or tissue cutting tip.

The intermediate elongate section 44 is adapted to slide within and relative to the sleeve as shown in FIGS. 1 and 2. The elongate section 44 fits (or plugs) the sleeve member. The size of the intermediate section may vary. An exemplary diameter (D2) of the intermediate section ranges from 0.090 to 0.102 inch and more preferably is about 0.100 inch. An exemplary length (L2) of the intermediate section is about 0.380 to 0.420 inch and more preferably about 0.400 inch.

The intermediate section 44 is shown terminating at a stop surface 48. The stop 48 arises from the geometry of the piercing tip 46 described above, and also acts to limit distal movement of the wings 14, and sleeve relative to the body 16. Additionally, as described herein, the suture lengths may be compressed against stop surface 48 increasing suture locking and retention.

Proximal section 42 is shown comprising a sacrificial area and means to connect to an insertion tool such as the insertion instrument 30 shown in FIGS. 1-2. In particular, the anchor body 16 shown in FIG. 3B includes a plurality of grooves 52 for receiving a threaded end of an insertion tool. Distal to the threads 52 is a weakened section 55 having a reduced diameter or thickness. As will be discussed further below, after the anchor is deployed and affixed in the bone, the insertion tool is retracted. The shaft shears or breaks away from the anchor assembly at the sacrificial region 55. The sacrificial region is adapted to break at a tension of about 80 to 100 pounds whereas the force required to slide the sleeve over the intermediate section of the anchor body is 15 to 60 pounds. Thus, it is a sacrificial section that predictably breaks, leaving the anchor assembly properly embedded in the bone. It is also to be understood, however, that a wide range of detaching means may be employed to detach the insertion instrument from the anchor. A non-limiting example of a detachment means is an internal threaded portion within the shaft. Upon application of sufficient stress between mating threaded portions, one or both of the threaded portions strip to release the anchor from the system. Additional examples include, without limitation, a frictional press-fit or barbed coupling may be employed. The amount of force required to separate the anchor from the deployment system is sufficiently high to minimize inadvertent deployment but also to ensure that the surgeon can deploy the anchor as desired.

Sleeve

FIGS. 4A-4D show a sleeve component 12 of an anchor assembly. Sleeve 12 is shown having a generally tubular shape and a lumen 62 extending from a proximal end 64 to a distal end 66 of the sleeve. The lumen is shown having a constant diameter (D3). An exemplary diameter (D3) for the sleeve 12 ranges from 0.105 to 0.120 inch and more preferably is about 0.108 inch. An exemplary length (L3) of the sleeve ranges from 0.160 to 0.350 inch and more preferably is about 0.250 inch.

As described herein, one of the functions of the sleeve is to lock the suture. In particular, sleeve coaxially surrounds a portion of the intermediate section 44 of the anchor body 16, and compresses a suture disposed therebetween.

Another function of the sleeve is to activate the bone lock or fix the anchor in the bone. The geometry of the sleeve enables bone locking. In particular, sleeve preferably has a tapered exterior. The outer diameter of the sleeve 12 increases in diameter from the distal end 66 to the proximal end 64. The diameter (D4) at the distal end may range from 0.130 to 0.150 inch and the diameter (D5) at the proximal end may range from 0.150 to 0.170 inch. The transition from the smaller diameter to larger diameter may be smooth, linear, or have a radius (R1). As discussed further below, urging sleeve into the bone affixation structure causes the affixation structure (e.g., the deflecting wings) to engage the bone.

Deflectable Wing Members

FIGS. 5A-5D show a bone locking or affixing structure 14. The bone locking component 14 is shown having three outwardly deflectable arms or wings 72. The arms extend from distal end section or base 75. The wings are separated by slots 74. In an application, the wings 72 are deflected to engage the bone and affix the anchor therein.

The bone locking structure 14 is shown having a generally tubular shape with a slight inward taper. In embodiments, and when undeployed, the outer diameter (D7) of the proximal end may range from 0.150 to 0.250 inch. In embodiments, the outer diameter (D8) of the distal end may range from 0.150 to 0.200 inch. Unlike the proximal end, the outer diameter of the distal end remains relatively constant and does not expand. In embodiments, the wall thickness (T) may range from 0.010 to 0.040 inch. Additionally, an exemplary overall length (L5) for the bone locking structure ranges from 0.160 to 0.400 inch and more preferably is about 0.330 inch. An exemplary length (L4) of the wings ranges from 0.100 to 0.350 inch and more preferably is about 0.270 inch.

In embodiments, the wings 72 collectively define an inner cavity 73. The deformable cavity 73 is sized and shaped to receive inner sleeve 12. As sleeve 12 is pushed into the cavity 73, the wing members 72 are forced to deflect and expand outwardly. The wing members 72 deploy and grip into the bone.

The amount of deflection may be characterized by, amongst other things, the difference in outer diameter (D7) of the bone locking structure between states, namely, the undeployed first state versus the deployed second state. An exemplary outer diameter (D7) of the proximal end when undeployed ranges from 0.160 to 0.180 inch and more preferably is about 0.160 inch. When deployed, the outer diameter D7 may expand to 0.240 to 0.260 inch or more. Consequently, the percent expansion in Area (A) ranges from 100 to 165%.

Additionally, as mentioned above, the degree or expansion is affected by bone quality. The wings tend to expand to a greater degree in softer bone. This is an advantage over static or fixed barbed anchor designs in which the diameter of the anchoring structure is fixed/constant irrespective of the bone quality.

The bone anchor structure is also shown having a base and distal aperture 75. Distal aperture 75 is sized to cooperate with the plug component 16. In particular, distal aperture 75 has a size and shape to receive the intermediate section 44 of the plug member 16. The distal aperture 75 is held fixed and against stop surface 48 of the plug component 16 so that further axial movement of the wings is prohibited as the sleeve is urged into cavity 73.

The distal end opening 75 remains constant. An exemplary distal end inner diameter (D9) ranges from 0.110 to 0.120 inch.

The bone locking component 14 may also comprise one or more openings or windows 76 to aid in providing space or room for the sutures. For example, window 76 is sized to carry or guide multiple sutures along the anchor body towards the distal end.

Barbs or ridges 80 are shown on the deflecting members 72. The ridges serve to grip the bone tissue. The change in height (or step) of the barbs or ridges ranges from 0.030 to 0.050 inch.

The illustration of the ridges is intended for example only. The suture anchor of the present invention may incorporate a number of features or structures to achieve a bone lock including, for example, assuming a larger profile using a variety of anchoring means such as expansion ribs, moly-bolts, rivets, wings, and other mechanisms. Variations are within the scope of the device and methods described herein. Additionally, variations include anchoring structures that do not fully encircle the anchor body, namely, partial or discontinuous ridges, ribs, and other structures. Also, the above mentioned size ranges and shapes are intended as exemplary only and the invention is not intended to be so limited except as recited in the appended claims.

Anchor Implantation Using Instrument

FIGS. 6-9 illustrate a suture anchor being implanted. As shown, sutures 28,29 may be previously stitched, connected to or looped through tissue 150 and loaded within anchor 132 (e.g., routed through the anchor using a snare) and instrument 128. Instrument 128 may also have lateral aperture or opening 140, located at the distal portion of the instrument but proximal to anchor wings 164, operable to allow passage of sutures 28, 29 from the instrument to the anchor. Sutures 28,29 may extend distally from aperture 140 within anchor 132, through eyelet, to the tissue 150, and return proximally along the same path and may be connected with a portion of the instrument handle (e.g., arms 172), to assist in managing the sutures 28,29 during insertion and tensioning.

The stitching process may be accomplished by any known means, and any known suture stitch may be employed. A stitch is desirably secured so that the suture is not inadvertently separated from the tendon after completion of the repair procedure, necessitating re-entry to the surgical site. In preferred approaches, the suture is attached to the soft tissue using a "mattress stitch," which is well known in the art as being a particularly secure stitch which is unlikely to fail postoperatively.

Anchor 132 may then be brought into contact against the underlying bone 100. The bone tissue 100 may be that of a shoulder, which comprises a humeral head, including an outer cortical bone layer 167, which is hard, and inner cancellous bone 169, which is relatively soft. As is typically the case for rotator cuff injuries, in this instance the supraspinatus tendon 150 has become separated from the humeral head. It is desirable to reattach the tendon 150 to the humeral head. Alternative rotator cuff repair procedures are also discussed in U.S. Pat. No. 6,524,317, and entitled "Method and Apparatus for Attaching Connective Tissues to Bone Using a Knotless Suture Anchoring Device", which is hereby incorporated by reference in its entirety.

Figure 7:
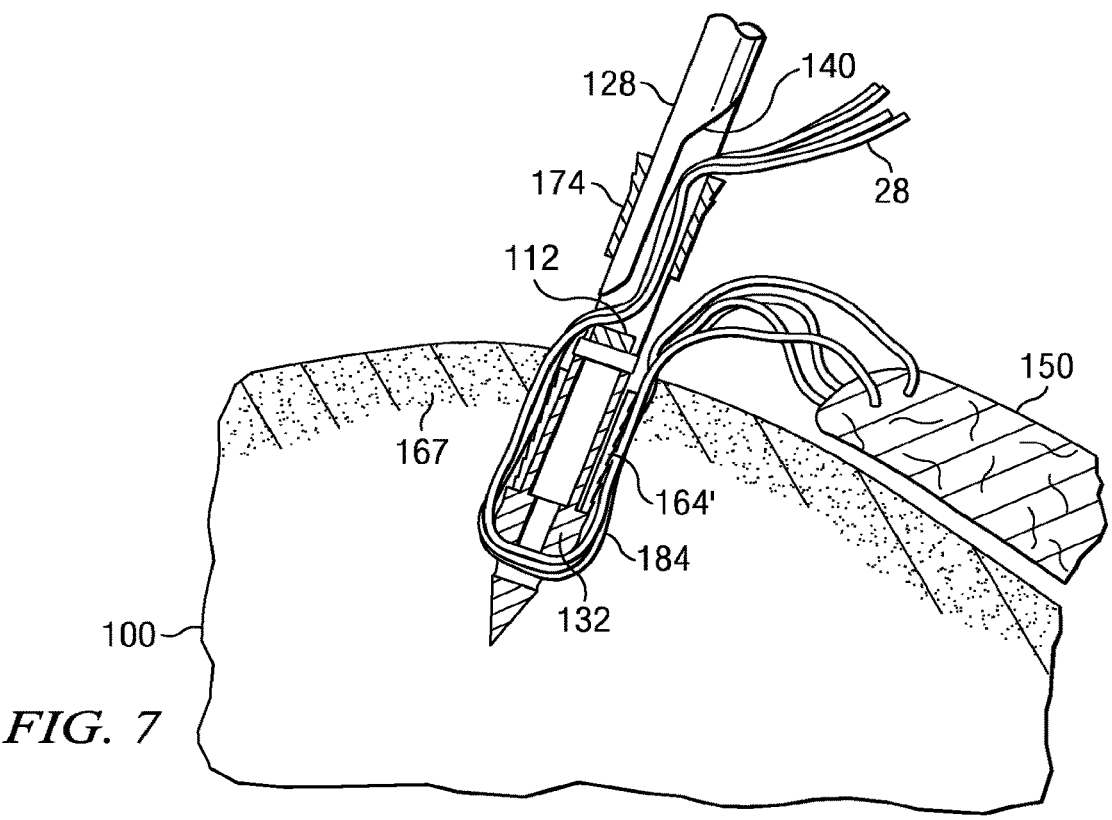
FIGS. 7 and 8 are partial cross sectional views of a suture anchor inserted in a bone in and undeployed and deployed configuration respectively.

Now with reference to FIG. 7, the proximal end of the instrument 128 or handle 130 may be tapped, e.g., by using a mallet, to drive the suture anchor 132 into the bone at a depth of, for example, approximately 6 mm. If viewed through an arthroscope, primary anchor 132 may be driven into the underlying bone 100 until an anchor depth indicator 112 (e.g., a colored marking or gradation) is visible just above or at the bone 100. Depth indicator 112 is a visual indicator to the user that the appropriate depth for anchor insertion has been reached. This may indicate that the anchor wings 164 have been inserted at the correct depth. Insertion to the cortical layer 167 is important to ensure anchoring structure 164' gains good purchase on the bone.

Figure 8:
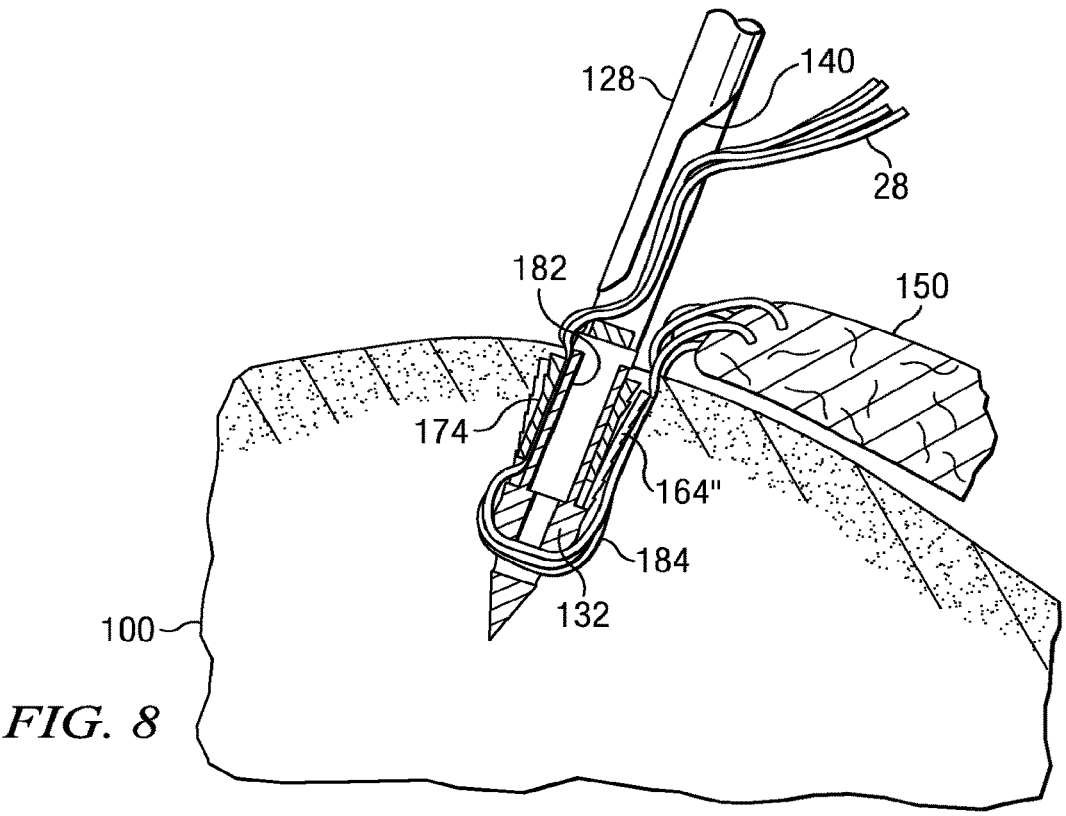

Next, tension is applied to the free legs 28 until the tendon 150 has been drawn toward the anchor as shown in FIG. 8, and is positioned for an anatomically proper repair and otherwise snugly situated with respect thereto. Non-limiting examples of threshold distances between the tissue 150 and the proximal end of the anchor range from 2-8 mm and more preferably 3-6 mm. The suture may be drawn by hand, by instrument, or a combination thereof.

With suture anchor 132 at a suitable depth, and the tissue in a desired position, the anchor wings 164 may be deployed within the bone 100, to lock the position of anchor 132 and to prevent anchor 132 from being pulled out of the bone 100. A die or driver member (not shown) of the instrument may push sleeve 174 distally and into the cavity of the anchoring structure, deflecting the wings 164" radially outward and into the bone.

Such action may be carried out in a number of ways. For example, a knob 168 shown in FIG. 6 may be linked to a driver or die member which, when turned, allows driver member to be advanced relative to the shaft. Advancing the driver member advances sleeve. The driver member may be advanced, for example, by pushing on it. Alternatively, a knob may be linked to a driver surface which is ratcheted distally, incrementally moving sleeve 174. Handles having various actuation mechanisms for deploying anchors are described in, e.g., U.S. Patent Publication Nos. 2008/0051836; 2009/0069823; and 2010/0191283, each of which is hereby incorporated by reference in its entirety.

Anchor 132 may then be released from instrument 128, which may be achieved by a variety of mechanical means as described above. For example, the components may be operable to have a weakness or failure point that fractures or disconnects upon application of a force or torque. Some methods for this release are described in U.S. Pat. No. 6,585,730, which is hereby incorporated by reference in its entirety. Additionally, the anchor may be implanted in other manners, and without a sophisticated instrument as described above.

Figure 9:
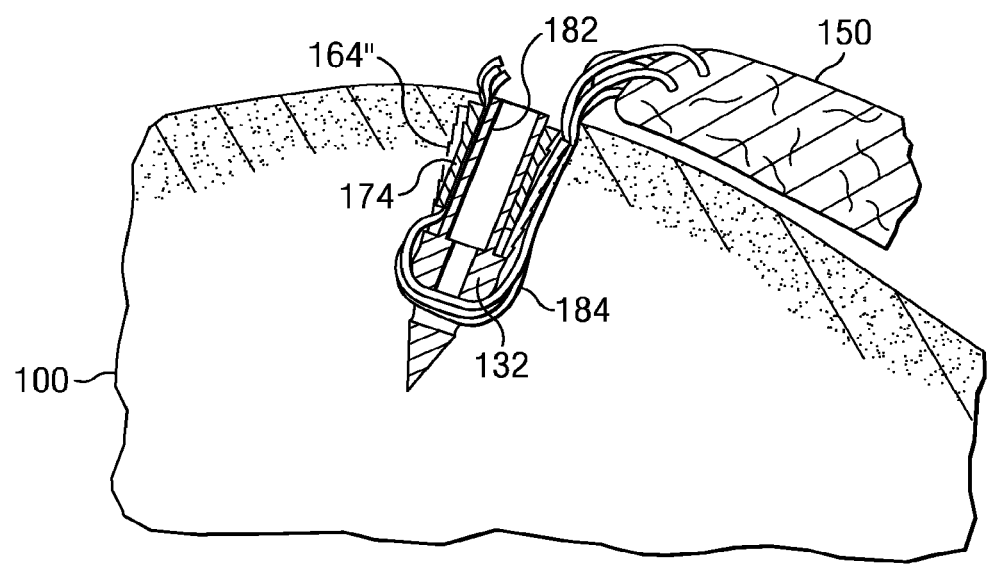
FIG. 9 is a partial cross sectional view of a suture anchor inserted in a bone in a deployed configuration and with the insertion instrument withdrawn.
Figure 10A:
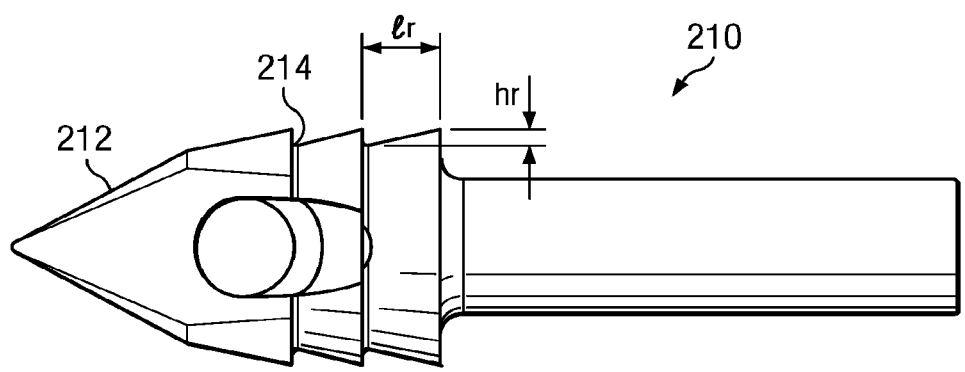
Figure 10B:
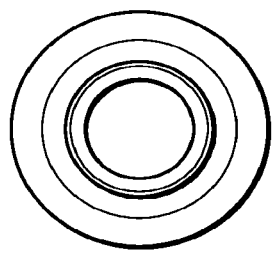

FIG. 9 shows a deployed anchor 100 situated within the bone 100 after release from the anchoring system. A first section of the suture 182 is secured within the anchor while a second section 184 is wedged between the cavity wall and an exterior of the anchor wings 164". In this variation, the suture loops from a first side of the anchor to a second side via a suture opening located in a tip portion of the locking plug. The suture is locked in several places: a) the suture is compressed between the anchor body shaft and the sleeve member; (b) the suture is compressed between the perpendicular stop surface of the body and the distal edge of the sleeve; and (c) the suture is compressed between the bone wall and the outer surface of the wing members. This so-called tri-lock provides safeguards against failure.

Alternative Embodiments

FIGS. 10A-10D show an alternative embodiment of a suture anchor component and in particular, an alternative embodiment of a locking plug 210. The locking plug 210 shown in FIGS. 10A-10D is similar to that shown above except that tip 212 includes ridges 214. The dimensions of the ridges are characterized by a ridge height $h_r$ ranging from 0.005 to 0.015 inch and a ridge length $l_r$ ranging from 0.030 to 0.050 inch. The ridges 214 aid in gripping bone as the locking plug is inserted (or pounded) into bone.

Figure 11B:
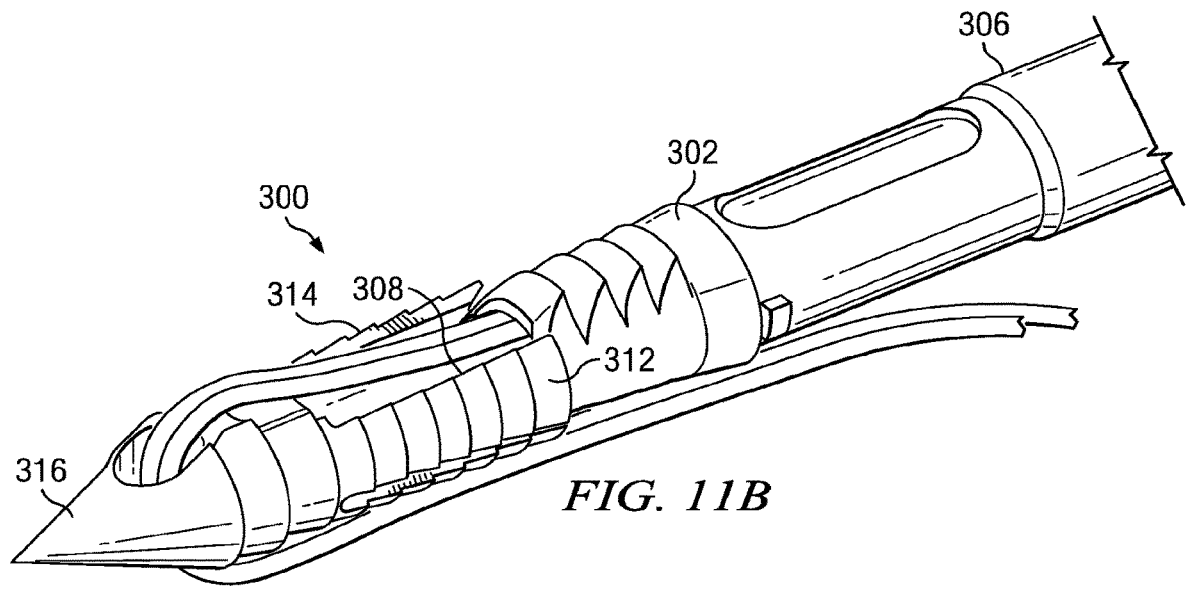
Figure 11C:
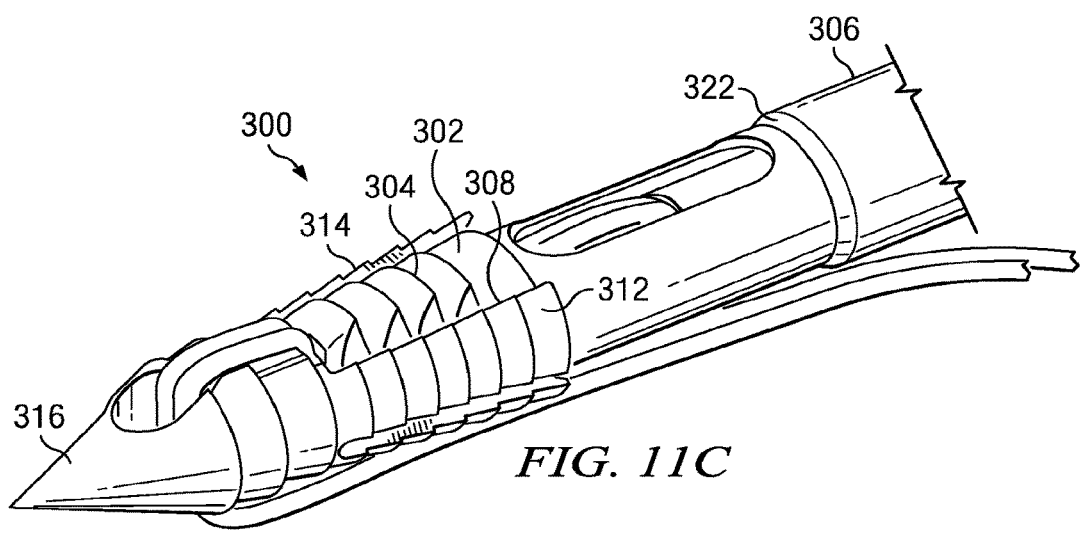

FIGS. 11A-11C show an alternative embodiment of a suture anchor assembly 300. The anchor 300 is similar to the anchors described above except that sleeve 302 includes a ridged section 304. With reference to FIG. 11B, the sleeve 302 is pushed distally by a driver member 306 along anchor plug member 316. In particular, driver 306 includes a push surface 322 which contacts proximal end of sleeve 302 to urge sleeve distally. FIG. 11C shows the ridged section of sleeve registered in the window 308 between the wings 312 and 314. The ridges 304 of sleeve supplement the bone locking to secure the anchor in the bone.

Methods for Securing Tissue

Figure 12:
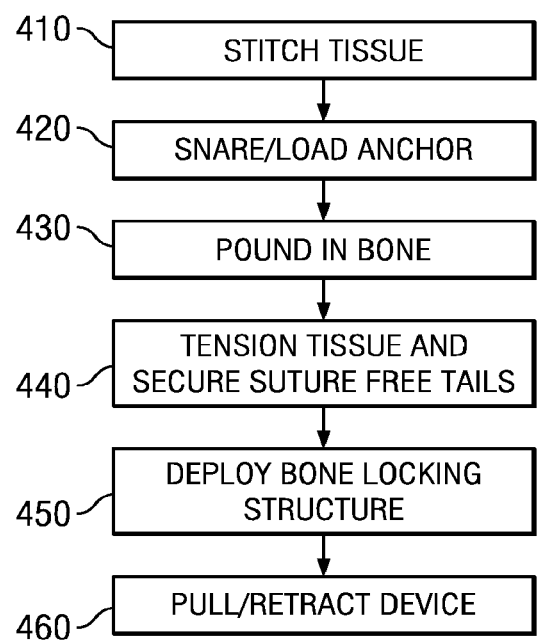
FIG. 12 is a flowchart of the steps to deploy a suture anchor.
Figure 6:
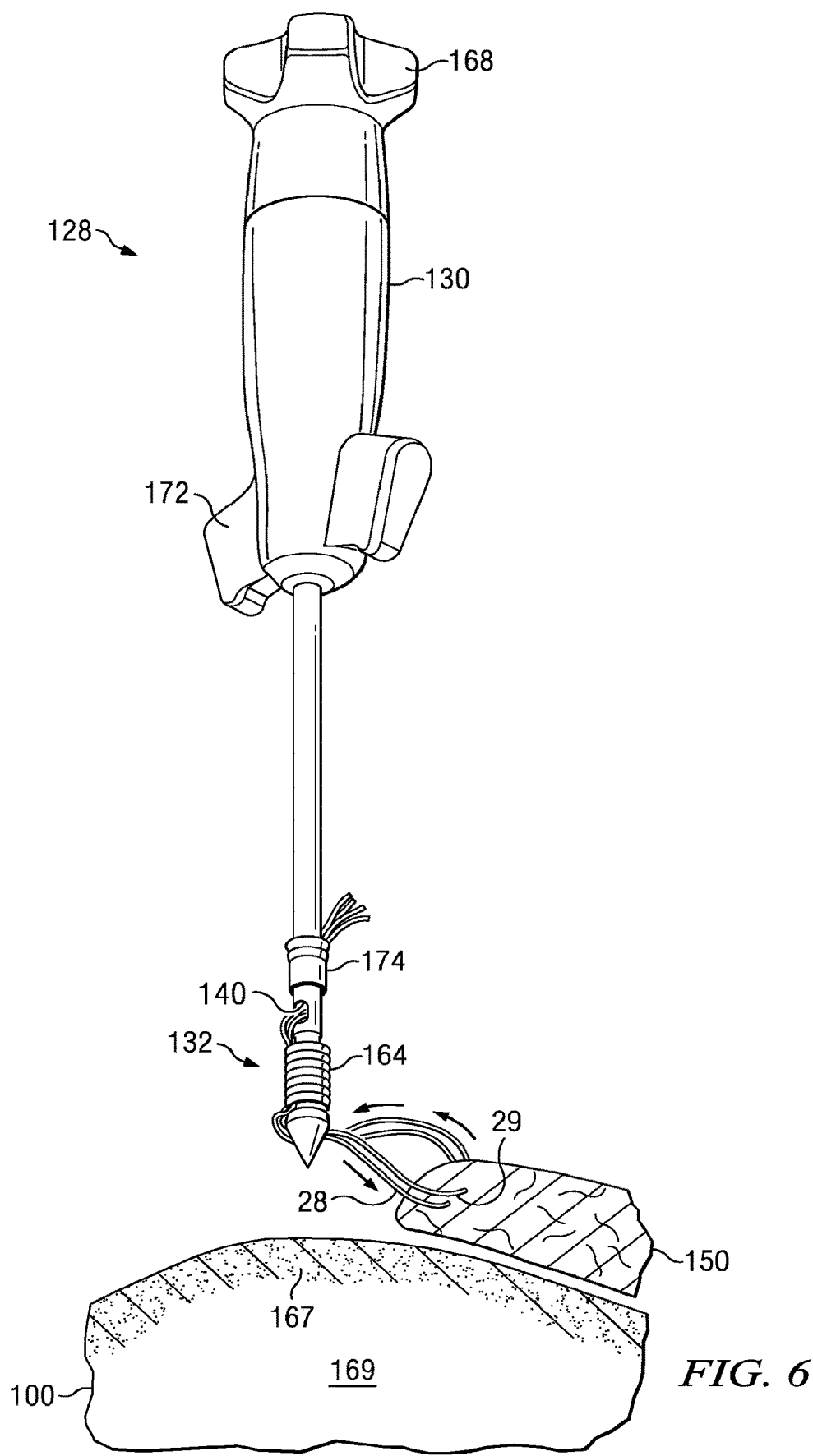
FIG. 6 is an illustration of a suture anchor system including a suture anchor and multiple sutures connected thereto.

FIG. 12 is a flowchart showing the steps of a medical procedure for securing connective tissue to bone. This procedure includes the steps of securing a bound limb of a length of one or more sutures to a portion of connective tissue (e.g., the rotator cuff tendon) to be attached to a portion of bone (e.g., the humeral head), using any method deemed suitable to the clinician (Step 410).

Step 420 states to load the length of suture through a suture anchor device. The suture anchor device may be temporarily attached to an insertion instrument shaft distal end, having an opening to provide a passage for the length of suture to gain access to the suture anchor device as described herein. The shaft distal end may also have a driver to deploy an anchoring element, disposed at the proximal end of the anchoring device.

Next, the suture anchor is inserted into a portion of bone, deep enough so that the anchor device proximal end is in the cancellous bone region. A marker or indicator may be present on the shaft distal end to aid in proper anchor placement. This step may be performed by hammering or pounding in the anchor with a mallet (430).

Step 440 states to apply tension to the free end of the length of suture so as to draw the bound limb of the length of suture toward the suture anchor device, thereby drawing the connective tissue closer to the anchor. The free end of the suture is drawn until the portion of connective tissue is snugly secured to the portion of bone.

The free suture ends may then be tied to a portion of the handle (or otherwise managed) to maintain tension for the next step.

Step 450 states to deploy the bone locking structure. This is preferably performed by pushing on the sleeve component with a driver of the insertion instrument so as to urge the sleeve into the annular space or cavity formed between the anchor plug component and the bone anchoring structure. The wings of the bone anchoring structure are deflected radially outward (flare outward) and into the tissue.

In embodiments, step 450 simultaneously locks the suture and detaches the inserter from the anchor body. In particular, the sleeve compresses the suture against the plug member, thereby locking the suture. The distal end of the sleeve pushes against stop surface 48 of the anchor body 16 causing the anchor body to detach along at a predetermined region such as engineered notch 55. In embodiments, an engineering notch between the anchor body and the end of the insertion instrument shaft breaks or shears at a predetermined force which is greater than the force necessary to deploy the sleeve.

Step 460 states to retract the insertion device. This may be carried out manually or semi automatically. First, the free ends of the suture are disconnected from the handle. Then, the handle is withdrawn.

In embodiments, the sacrificial region between the anchor plug and the end of the insertion instrument shaft breaks or shears at a predetermined force which is less than the force necessary to pull out the embedded anchor.

The suture ends may then be trimmed close to the proximal end of the embedded anchor.

Figure 13A:
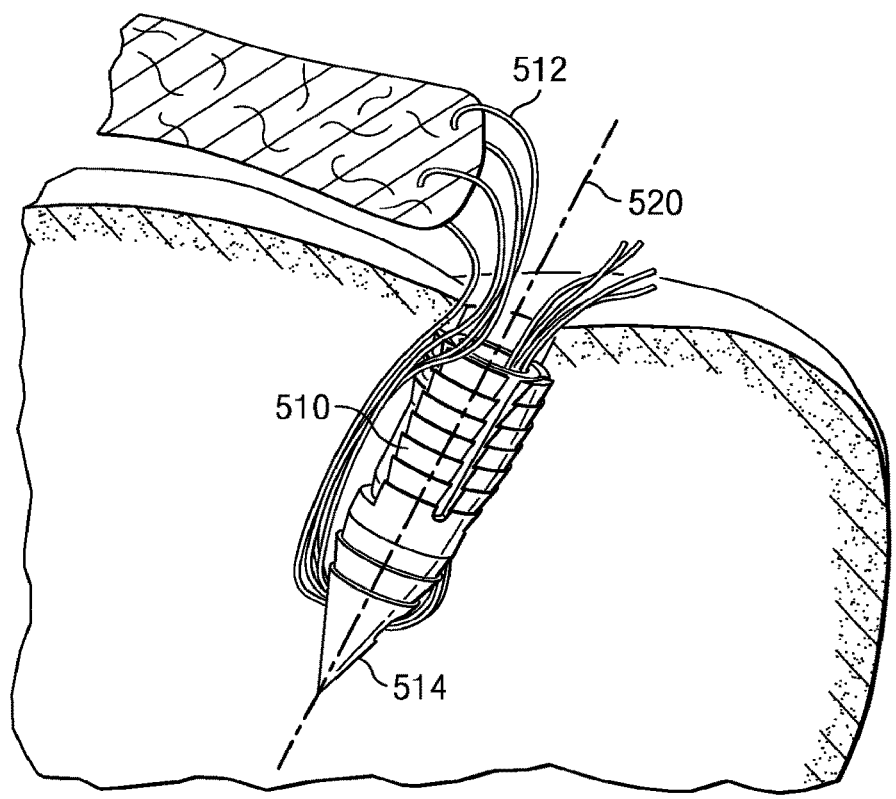
FIGS. 13A and 13B are illustrations of a suture anchor in bone in an aligned position and an offset position respectively.
Figure 13B:
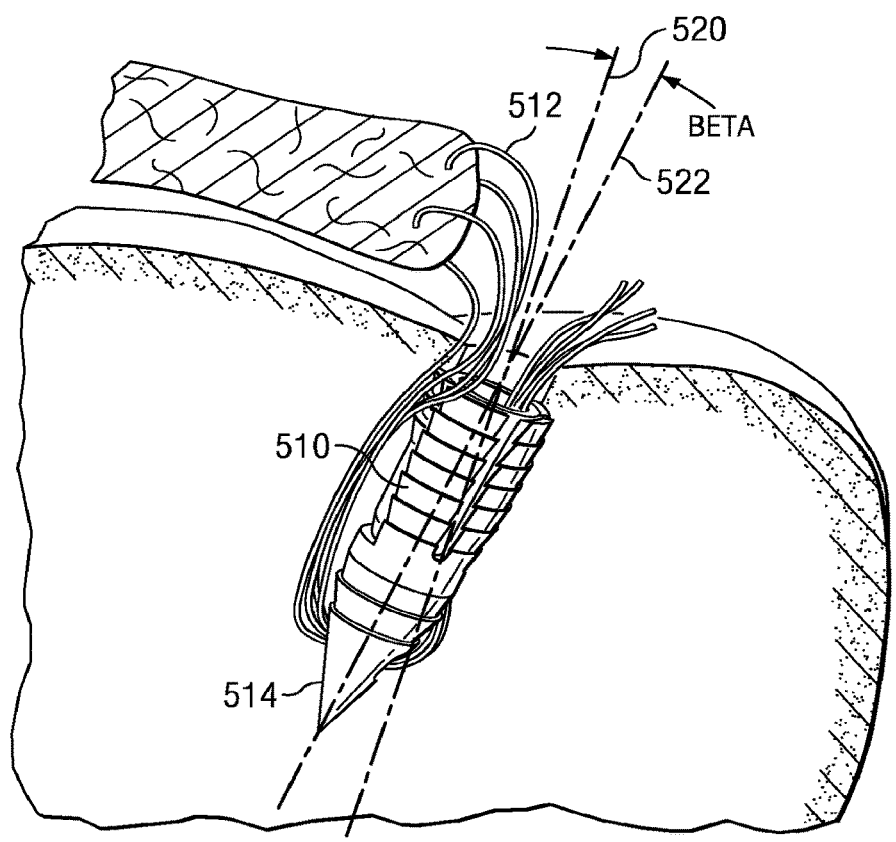

FIGS. 13A and 13B show another anchor 510 deployed in a bone. The anchor is shown having an offset or tilt angle (β). The tissue side of the sutures 512 engage the anchor 510 at the distal end section, namely, the distal tip eyelet 514. Tension, applied to the tissue or bound side of the sutures, induces a shift or off-axis force to the anchor (rather than pull out the anchor axially). The angle or degree of toggle (Beta) desirably ranges from 0 to 15 degrees and more preferably is between 5 and 10 degrees. Tension on the bound suture limb may be applied manually by the surgeon, or may result from exercise and use of the tendon post operation.

Without being bound to theory, the toggle or tilt from the first position 520 to the second position 522 is different than most other anchors having the sutures extend through and down the center of the anchor. When the sutures extend down the center of the anchor, tension from the tissue (or repeated use of the tissue) acts to pull out the anchors. In the present embodiment shown in FIGS. 13A and 13B, tension or strain on the anchor acts to toggle or tilt the anchor, further embedding the anchor in the bone.

Although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A suture anchor for securing soft tissue to bone with at least one suture, wherein the suture anchor is selectively deployed to fix the suture anchor in bone, said suture anchor comprising:
   an eyelet for receiving the at least one suture therethrough;
   a plurality of deflecting sections disposed on an outer surface of the suture anchor, wherein an inner surface of the plurality of deflecting sections defines a cavity, the cavity having a bottom surface proximally separated from the eyelet; and
   a deployment sleeve having an open-ended distal end, a distal-most end of the open-ended distal end configured to cooperate with the inner surface of the plurality of deflecting sections to deflect the plurality of deflecting sections to engage bone.

2. The suture anchor of claim 1 wherein the plurality of deflecting sections is deflectable to a plurality of different sizes.

3. The suture anchor of claim 1 wherein the plurality of deflecting sections deflects outwardly from the suture anchor when the deployment sleeve is urged into said cavity.

4. The suture anchor of claim wherein the plurality of deflecting sections comprises at least three discrete wings.

5. The suture anchor of claim 1 wherein the suture anchor is a biocompatible polymer.

6. The suture anchor of claim 1 wherein the cavity is an annular space.

7. The suture anchor of claim 1 wherein the deployment sleeve comprises a plurality of ridges extending circumferentially around the deployment sleeve, at least some of the plurality of ridges configured to engage bone.

8. A suture anchoring system for anchoring a length of suture with respect to a bone, comprising:
   an anchor insertion instrument comprising a handle, and an elongate rigid shaft extending distally from the handle, said shaft comprising a distal end section;
   a suture anchor selectively detachably coupled directly to the shaft distal section, the suture anchor comprising an eyelet and a deflectable bone anchoring structure defining a cavity, with a bottom surface proximally separated from the eyelet; and
   a deployment sleeve disposed around the shaft distal end section, the deployment sleeve having a distal-most end configured to axially translate relative to the deflectable bone anchoring structure to enter the cavity, and radially deflect the bone anchoring structure.

9. The system of claim 8, wherein the shaft distal section threadingly couples to the suture anchor and is configured to selectively strip upon the application of sufficient stress so as to selectively detach the suture anchor from the insertion instrument.

10. The system of claim 8 further comprising a snare extending through at least a portion of the insertion instrument and the eyelet of the suture anchor such that when a distal portion of the snare is affixed to a length of suture, withdrawal of the snare pulls the length of suture through the eyelet and the distal portion of the insertion instrument.

11. The system of claim 8 wherein the suture anchor defines a tapered distal most tip.

12. The system of claim 8 wherein the bone anchoring structure has a plurality of deflectable wings, and each wing comprises a plurality of exterior ridges.

13. The system of claim 8 wherein the deployment sleeve comprises a plurality of exterior ridges extending circumferentially around the deployment sleeve, the exterior ridges configured to engage the bone.

14. The suture anchor of claim 1 wherein the deployment sleeve is configured to move from an undeployed configuration to a deployed configuration that secures the at least one suture against an outer surface of the deployment sleeve.

15. The suture anchor of claim 14 wherein in the undeployed configuration, the deployment sleeve distal-most end is proximally spaced from the plurality of deflecting sections.

16. The suture anchor of claim 1 wherein the deployment sleeve distal-most end enters the cavity to cooperate with the inner surface of the deflecting sections to deflect the plurality of deflecting sections.

17. The system of claim 1, wherein the suture anchor is coupled to an insertion instrument distal section with threads, the threads configured to selectively strip upon the application of sufficient stress so as to selectively detach the suture anchor from the insertion instrument distal end.

18. The suture anchoring system of claim 8 wherein the deployment sleeve is configured to move from an undeployed configuration to a deployed configuration to knotlessly secure the length of suture and wherein in the undeployed configuration, the entire deployment sleeve proximally spaced from a proximal-most end of the deflectable bone anchoring structure.

19. A suture anchoring system for anchoring a length of suture with respect to a bone, comprising:
   an anchor insertion instrument comprising a handle, and an elongate rigid shaft extending distally from the handle, said shaft comprising a distal end section;
   a suture anchor selectively detachably coupled directly to the shaft distal section, the suture anchor comprising an eyelet and a deflectable bone anchoring structure defining a cavity, with a bottom surface proximally separated from the eyelet; and
   a deployment sleeve disposed around the shaft distal end section, the deployment sleeve configured to axially translate relative to the deflectable bone anchoring structure and radially deflect the bone anchoring structure;
   wherein the shaft distal section threadingly couples to the suture anchor and is configured to selectively strip upon the application of sufficient stress and selectively detach the suture anchor from the insertion instrument.

20. The suture anchoring system of claim 19 wherein the deployment sleeve is configured to move from an undeployed configuration to a deployed configuration to knotlessly secure the length of suture and wherein in the undeployed configuration, the entire deployment sleeve proximally spaced from a proximal-most end of the deflectable bone anchoring structure.

* * * * *